United States Patent [19]

Raggiotti et al.

[11] 4,031,365

[45] June 21, 1977

[54] TEMPERATURE MONITORING AND DISPLAY SYSTEM

[75] Inventors: Guglielmo Raggiotti; Domenico Colonnelli, both of Perugia, Italy

[73] Assignee: Itus Patent Holding (IPH) N.V., Willemstad, Netherlands Antilles

[22] Filed: Oct. 14, 1975

[21] Appl. No.: 621,915

[30] Foreign Application Priority Data

Aug. 21, 1975 Italy .................................. 51020/75

[52] U.S. Cl. .......................... 235/151.3; 73/362 R; 128/2 H; 235/92 MT
[51] Int. Cl.² ....................... G01V 1/28; G01K 7/00
[58] Field of Search .................. 235/151.3, 92 MT; 128/2 H, 2.1 R, 2.1 E; 73/362 R, 362 AR; 331/66

[56] References Cited

UNITED STATES PATENTS

| 2,927,463 | 3/1960 | Stubbs | 128/2 H |
|---|---|---|---|
| 3,601,586 | 8/1971 | Slavin | 235/92 MT |
| 3,834,238 | 9/1974 | Mueller et al. | 235/92 MT |
| 3,872,728 | 3/1975 | Joyce et al. | 73/362 AR |

OTHER PUBLICATIONS

Keefe, E. F.; "A Practical Open-Scale Thermometer for Timing Human Ovulation", New York State Journal of Medicine, vol. 49, No. 21, 11/1/49, pp. 2554-2555

Klaften, E.M.; "Utero-Thermometry; A Study of Uterine Temperature During Reproductive Life, Menopause, and Amenorrhea"; Journal of Clinical Endocrinolocy; vol. 4, 4/1944, pp. 159-165.

Primary Examiner—Charles E. Atkinson
Assistant Examiner—Errol A. Krass
Attorney, Agent, or Firm—John J. Byrne

[57] ABSTRACT

A system is provided for continuously monitoring and displaying temperature levels of a patient which is particularly adapted to indicate the ovulation activity of a female through monitoring the temperature variations of the body of the patient during the menstrual cycle. The system includes a transducer, such as a thermistor, for producing an output voltage in accordance with the temperature sensed, a voltage controlled oscillator for producing an output whose frequency varies in accordance with the output voltage of the thermistor, and a binary coded counter, controlled by the system clock, which produces a four-bit digital output representative of the measured temperature. The output of the counter during each cycle is stored in a shift register and after N cycles, an analog voltage representative of the arithmetic average for the N cycles is compared with an analog voltage corresponding to the output for the N + 1 cycle. An abnormal condition is indicated when the output signal deviates from a reference by a predetermined amount and an alarm is activated if the abnormal condition is indicated for a predetermined number of cycles.

12 Claims, 1 Drawing Figure

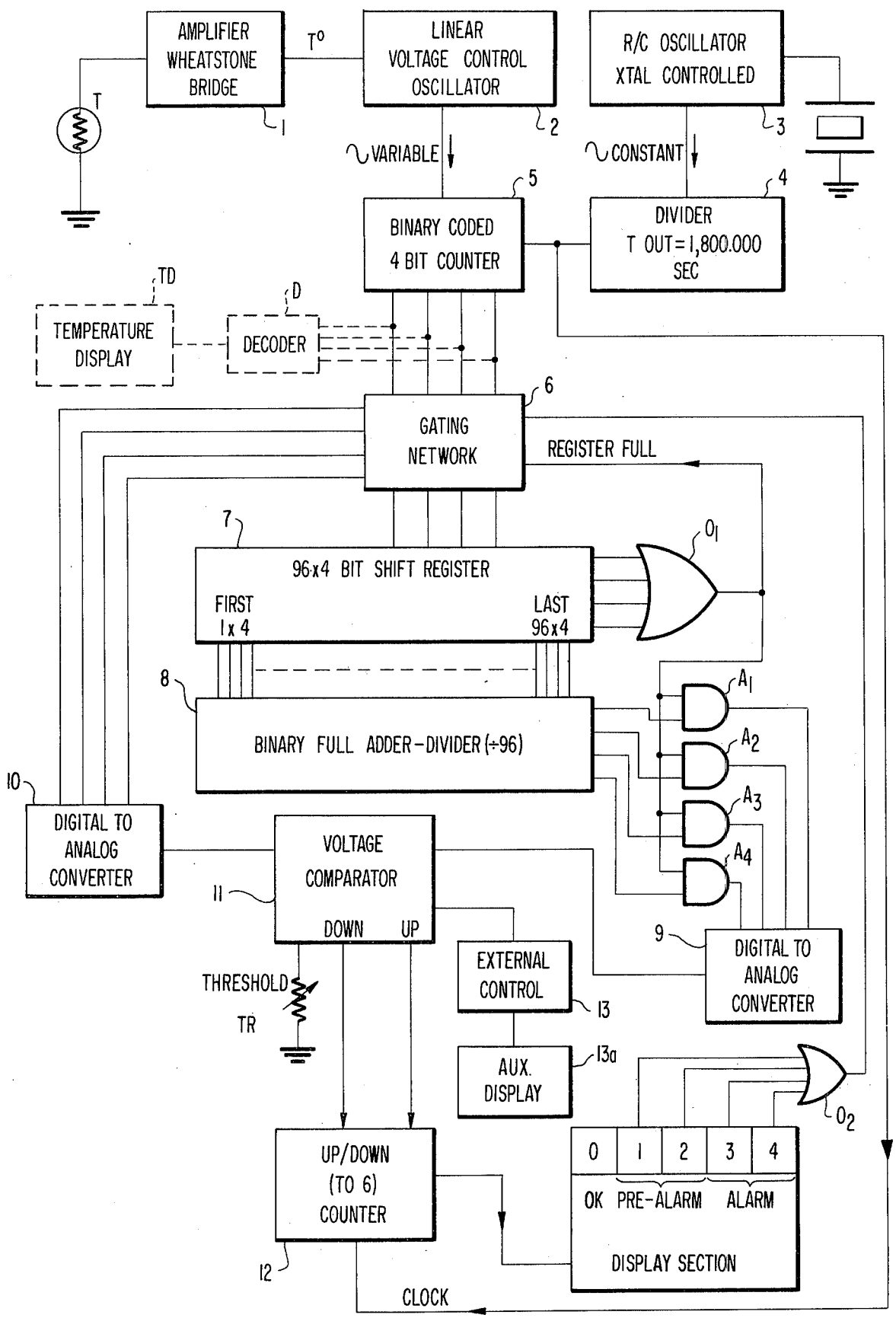

TEMPERATURE MONITORING AND DISPLAY SYSTEM

FIELD OF THE INVENTION

The present invention relates to a temperature monitoring and display system which can be utilized, for example, to monitor the body temperature of a female patient during ovulation. The system is of general application and can be used in monitoring and controlling any temperature cycle regardless of duration, with any desired degree of accuracy.

SUMMARY OF THE INVENTION

The present invention provides for monitoring, storing and displaying information related to the temperature levels of the body of a patient and, as referred to hereinabove, is principally adapted to monitor ovulation by monitoring the body temperature of a female patient throughout the menstrual cycle.

In accordance with a preferred embodiment thereof, the system of the inveention includes a sensor-transducer for producing an electrical output voltage in accordance with the temperature sensed, a voltage controlled oscillator for producing an output whose frequency varies in accordance with the transducer voltage output and a counter, connected to the voltage controlled oscillator and to a system clock, for producing a binary coded digital output representative of the temperature measured. An N-output shift register under the control of a gate circuit stores the output of the counter during N cycles (N = 96 in a specific embodiment) and an adder-divider circuit connected to the shift register adds the N outputs and divides by N so as to produce an output proportional to the arithmetic means of the N outputs. During the N + 1 cycle, the output of the counter is routed by the gate circuit to a digital-to-analog (D/A) converter. A voltage comparator compares the output of the D/A converter to that of a further D/A converter connected to the output of the adder-divider circuit. When the difference between the signals positively exceeds a preselected reference level, an abnormal indication is provided. The comparator drives an up-down counter which is connected to a display unit. The latter includes an alarm which is actuated when an abnormal indication is produced during a predetermined number of cycles.

The system of the invention can be implemented on a single chip using LSI techniques, employing CMOS and/or MOS circuitry. The system thus can be made to be very rugged and compact, permitting its continuous use over periods of years. The system is readily portable and has very low power requirements.

Other features and advantages of the invention will be set forth, or apparent from, the detailed description of a preferred embodiment found hereinbelow.

BRIEF DESCRIPTION OF THE DRAWINGS

The single FIG. in the drawings, is a schematic, block-form circuit diagram of a monitoring system in accordance with a preferred embodiment of the invention.

DESCRIPTION OF THE PREFERRED EMBODIMENT

Referring to the single figure in the drawings, a thermistor T is used to measure or detect the body temperature of the patient under observation. Thermistor T produces a voltage which varies with the temperature measured in accordance with a pseudo-linear lao for temperatures between about 36.0° and 37.6° C. This voltage is detected and amplified by a Wheatstone Bridge-amplifier 1. The output of amplifier-bridge 1 is connected to a linear voltage controlled oscillator (VCO) 2 which produces an output whose frequency varies in accordance with the voltage input thereto. The output of VCO 2 forms one input to a binary-coded, four-bit counter 5.

A crystal controlled oscillator 3 produces a stabilized reference frequency which is divided by a divider 4 to produce the control input to counter 5. As a compromise between the need to place the controls as close together as possible and the desire to eliminate possible interference by outside temperature sources, a control frequency of 48 cycles per day (one cycle per 1,800,000 seconds) has been selected in accordance with a preferred embodiment. Under these circumstances it is possible to produce a voltage output which is accurate within one-tenth of one degree Centigrade within the measuring range of interest. It has been found that accuracy is excess of this figure is unnecessary for present purposes. However, it should be noted that to increase the accuracy of the system to one-hundreth of one degree Centigrade by simply adding an additional significant bit to the system.

The temperature detected by thermistor T, as presented in the four-bit binary coded output of counter 5, is stored in a shift register 7 under the control of gating network or gate 6.

Shift register 7 is a series-parallel, four-bit in, 96-bit out, register which produces 96 columns of four bits. The first storage cycle takes place during a period prior to the thermal measurement of interest and the register stores 96 four-bit binary coded numbers corresponding to the normal temperature condition of the subject over a complete 2 day period of time. When the 96 numbers are stored, the shift register 7 transfers the stored data to an adder-divider 8 which totals the 96 numbers and divides by 96 so as to produce an output in accordance with the arithmetic average of the 96 numbers stored. At this time, gate 6 inhibits the input to register 7 so that, during the 97th cycle, the output of counter 5 is connected through gate 6 to a digital-to-analog (D/A) converter 10 which produces an analog output voltage corresponding to the digital output of the counter 6. Gate 6 is controlled by a four input OR gate $O_1$ which, when the 96th number is stored, triggers gate 6 to inhibit the input from counter 5 from loading register 7 until a feedback signal from a second OR gate $O_2$ indicates that the last number can be stored thereby erasing the first number stored. The output of OR gate $O_1$ is also connected to one input of a series of four AND gates $A_1$ to $A_4$. A further D/A converter 9 is connected to the output of adder-divider 8 through AND gates $A_1$ to $A_4$ and produces an analog voltage output corresponding to the digital output of adder-divider 8 and hence to the arithmetic average of the previous 96 temperature measurements over the 2 day period in question. Gating out of the output of binary adder-divider is controlled by OR gate $O_1$ and occurs when the 96th number is stored.

The outputs of D/A converters 10 and 9 are compared by a voltage comparator 11 whose threshold input level is set so that the comparator 11 will be energized only when the input thereto deviates by a selected, positive amount from a predetermined reference level as set by a threshold resistor TR. Comparator 12 is also connected to an external control circuit 13. The purpose of control circuit 13 is to provide a check of the body temperature and an auxiliary dislay 13a connected to the output of control circuit 13 produces a suitable display. The control circuit can be permanently wired into the system or can be push-button operated, depending on power requirements. The output of comparator 10 is connected to a bi-directional or up/down counter 12 which also receives clocking pulses from divider 4. Bidirectional counter 12 has a six-bit capacity and includes a "normal" and an "abnormal" input.

The output of counter 12 is connected to a display or indicator circuit 14. Display 14 is preliminarily set to indicate a normal or "OK" condition. If the comparator produces an abnormal output during the comparison cycle referred to above, thereby indicating an abnormal condition, counter 12 will cause the display 14 to move to the "1" or pre-alarm position. Similarly, depending on whether or not the succeeding inputs are within the prescribed limits, display 12 will move towards the "O" or "OK" level or towards the "4" or alarm level. Deviations of the input signals around "O" or normal (average) level will be related to more or less normal temperature variations such as produced by external causes. However, a rapid and continuous increase in the direction of deviation of input signals, corresponding to a rapid, continuous increase in temperature, is an indication that the patient is being affected by phenomena of the type which is to be isolated and investigated.

Under conditions where an abnormal condition is indicated, shift register 7 is blocked or inhibited by an inhibit signal transmitted through OR gate $O_2$ connected to the "1", "2", "3", and "4" outputs of display. For indications corresponding to temperatures between the preselected limits, i.e., normal indications, the information stored by register 7 in constantly updated so that the latest data corresponding to the temperatures measured replaces the data previously stored. In this way the average temperature used in comparison operation described above will be a slowly changing variable with time and will vary in accordance with various factors, either climatic or biological, related to the age, metabolism or other neuro-vegetative characteristics of hte patient.

The alarm of display 14 is self-sustaining throughtout a complete information cycle (5 cycles in the embodiment under consideration) so as to ensure that the alarm is activated during the time of occurrence of the phenomenon causing the alarm.

It is noted that there is a margin of uncertainty in the operation of the system related to the fact that as much as two consecutive one-half hour intervals can be required for the display to move from "0" to "1" or pre-alarm. This interval has been found to be acceptable particularly as related to an approximate 28-day cycle since an accuracy is provided of about one parts in 1344.

A temperature display TD and a decoder D, indicated in dashed lines, may be connected to the output of counter 5 to provide a direct temperature reading.

The system of the invention is preferably implemented on a single chip using LSI (large scale integrated circuit) techniques and employing CMOS circuits.

Although the invention has been described relative to a preferred embodiment thereof, it will be appreciated by those skilled in the art that variations and modifications can be effected in the embodiment without departing from the scope and spirit of the invention.

We claim:

1. A monitoring system for monitoring the temperature levels of the body of a patient for extended periods, said system comprising:
   transducer means for sensing the temperature of the body of the patient under observation and for producing an output voltage in accordance therewith,
   a voltage controlled oscillator for producing an output whose frequency varies in accordance with the output voltage of said transducer means,
   an n-bit binary coded counter connected to said voltage controlled oscillator for producing an n-bit binary coded output representative of the temperature sensed,
   gating means,
   a shift register controlled by said gating means for storing the n-bit binary coded output of said counter over N cycles, said N cycles being repeated and said counter producing an N + 1 output following the Nth output thereof,
   an adder-divider circuit connected to the outputs of said register for summing N outputs stored thereby and for dividing the resultant sum by N to produce a digital signal representative of the arithmetic average of said N outputs,
   comparator means for comparing the output of said adder-divider circuit with the N + 1 output of said counter and for producing a first "normal" output when the difference between said outputs is less than a positive threshold level and for producing a second "abnormal" output when said difference exceeds said threshold level, and
   display means connected to the output of said comparator means.

2. A system as claimed in claim 1 further comprising a first digital-to-analog converter connected to the output of said counter through said gating means for converting the N + 1 output of said counter into a corresponding analog voltage and a second digital-to-analog converter for converting the digital output signal produced by said adder-divider circuit into a corresponding analog voltage, said comparator means comparing said analog voltages and said system further comprising an up-down counter connected between said voltage comparator and said display means.

3. A system as claimed in claim 1 wherein said transducer means comprises a thermistor.

4. A system as claimed in claim 2 further comprising Wheatstone Bridge-amplifier means connected between said thermistor and said voltage controlled oscillator.

5. A system as claimed in claim 2 wherein display means includes alarm means which is actuated when an "abnormal" output is produced by said up-down counter for a predetermined number of cycles.

6. A system as claimed in claim 2 further comprising means for generating a clock frequency for controlling said binary coded counter and said up-down counter.

7. A system as claimed in claim 6 wherein said clock generating means includes a crystal controlled oscillator and a divider circuit.

8. A system as claimed in claim 1 wherein said gating means provides constant updating of the information stored by said register, said system including means for connecting said display means to said gating means for inhibiting updating of said register when an abnormal condition is indicated.

9. A system as claimed in claim 1 wherein N = 96, said n-bit counter comprising a four-bit counter and said shift register provides 96 four-bit outputs, said clock generator producing one clock pulse every 1,800 seconds.

10. A system as claimed in claim 1 further comprising temperature display means connected to the output of said binary coded counter.

11. A monitoring system for monitoring the temperatures of a patient for extended periods of time, said monitoring system comprising:

transducer means for continuously sensing the temperature of the patient and for producing an output in accordance therewith, means for converting the output of said transducer means into a digital signal representative of the temperature sensed by said transducer means, means connected to said converting means for storing the said digital signal produced by said converting means over N cycles to produce N stored signals, means connected to said storage means for summing the amplitudes of the said signals stored by said storage means over N cycles and for dividing the sum of said signals by N so as to produce an output signal representative of the arithmetic average of said digital signal over N cycles, means for generating a reference signal, means connected to the output of said summing and dividing means for comparing the output signal produced by said summing and dividing means with said reference signal and for producing a first, "normal" output when the difference between said signals is less than a predetermined value and for producing a second, "abnormal" output when said difference exceeds said predetermined value, and indicator means connected to the output of said comparing means for providing an indication of the results of said comparison.

12. A monitoring system as claimed in claim 11 wherein said converting means comprises a voltage controlled oscillator connected to the output of said transducer means and counter means for producing an output signal in accordance with the frequency output of said oscillator, said counter means producing an N + 1 output following the Nth output thereof, said system further comprising gating means and said reference signal generating means comprises means responsive to said gating means for receiving the N + 1 output of said counter means and for generating said reference signal in accordance therewith.

* * * * *